United States Patent
Kobayashi et al.

(10) Patent No.: US 11,857,310 B2
(45) Date of Patent: Jan. 2, 2024

(54) PHYSIOLOGICAL PARAMETER PROCESSING APPARATUS

(71) Applicant: NIHON KOHDEN CORPORATION, Tokyo (JP)

(72) Inventors: Hironori Kobayashi, Tokorozawa (JP); Yukio Nonaka, Tokorozawa (JP); Kazuri Higashi, Tokorozawa (JP); Takayuki Sugiyama, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 282 days.

(21) Appl. No.: 15/992,809

(22) Filed: May 30, 2018

(65) Prior Publication Data

US 2018/0344206 A1    Dec. 6, 2018

(30) Foreign Application Priority Data

May 31, 2017  (JP) ................. 2017-108750

(51) Int. Cl.
*A61B 5/083*    (2006.01)
*A61B 5/08*     (2006.01)
(Continued)

(52) U.S. Cl.
CPC ............. *A61B 5/083* (2013.01); *A61B 5/08* (2013.01); *A61B 5/082* (2013.01); *A61B 5/087* (2013.01); *A61B 5/0826* (2013.01); *A61B 5/0878* (2013.01); *A61B 5/4806* (2013.01); *A61B 5/4818* (2013.01); *A61B 5/7203* (2013.01);
(Continued)

(58) Field of Classification Search
CPC .......... A61B 5/083; A61B 5/08; A61B 5/082; A61B 5/0826; A61B 5/087; A61B 5/0878; A61B 5/4806; A61B 5/4818; A61B 5/7203; A61B 5/7275; A61B 5/741; A61B 5/742;
(Continued)

(56) References Cited

U.S. PATENT DOCUMENTS 6,165,133 A    12/2000    Rapoport et al.
2004/0149282 A1    8/2004    Hickle
(Continued)

FOREIGN PATENT DOCUMENTS

EP    2 668 900 A1    4/2013
JP    2000-500379 A    1/2000
(Continued)

OTHER PUBLICATIONS

Al-Khalidi, Farah Q., et al. "Respiration rate monitoring methods: A review." Pediatric pulmonology 46.6 (2011): 523-529. (Year: 2011).*

(Continued)

*Primary Examiner* — Alex M Valvis
*Assistant Examiner* — Chanel J Jhin
(74) *Attorney, Agent, or Firm* — Pearne & Gordon LLP (57) ABSTRACT

A physiological parameter processing apparatus includes an input interface section that acquires respiration data produced based on a respiratory gas that is obtained from at least one of a mouth and nose of a subject, and an analyzing section that analyzes in real time the respiration data acquired through the input interface section, and that produces analysis result data which can be displayed in real time.

17 Claims, 5 Drawing Sheets (51) Int. Cl.
  *A61B 5/00* (2006.01)
  *A61B 5/087* (2006.01)
  *G16H 50/30* (2018.01)
  *A61B 5/097* (2006.01)

(52) U.S. Cl.
  CPC ............ *A61B 5/7275* (2013.01); *A61B 5/741* (2013.01); *A61B 5/742* (2013.01); *A61B 5/746* (2013.01); *A61B 5/0816* (2013.01); *A61B 5/097* (2013.01); *G16H 50/30* (2018.01)

(58) Field of Classification Search
  CPC ....... A61B 5/746; A61B 5/0816; A61B 5/097; G16H 50/30
  USPC .......................................................... 600/532
  See application file for complete search history.

(56) References Cited

U.S. PATENT DOCUMENTS

| | | | |
|---|---|---|---|
| 2006/0270941 A1* | 11/2006 | Xie | A61B 5/0816 600/529 |
| 2007/0107728 A1* | 5/2007 | Ricciardelli | A61B 5/083 128/204.22 |
| 2012/0125337 A1* | 5/2012 | Asanoi | A61B 5/0816 128/204.23 |
| 2013/0324877 A1 | 12/2013 | Nonaka et al. | |
| 2015/0005658 A1 | 1/2015 | Nonaka et al. | |
| 2016/0210747 A1* | 7/2016 | Hay | G06F 3/04847 |
| 2017/0035325 A1 | 2/2017 | Oaki et al. | |
| 2018/0153427 A1* | 6/2018 | Al-Jumaily | A61B 5/021 |

FOREIGN PATENT DOCUMENTS

| | | |
|---|---|---|
| JP | 2005-137479 A | 6/2005 |
| JP | 2013-248011 A | 12/2013 |
| JP | 2015-008925 A | 1/2015 |
| JP | 2017-035473 A | 2/2017 |
| WO | 2015/063834 A1 | 5/2015 |
| WO | 2016/179651 A1 | 11/2016 |

OTHER PUBLICATIONS

NPL Cao et al (Cao, Zhe, Rong Zhu, and Ruiyi Que. "Low-cost portable respiration monitor based on micro hot-film flow sensor." 2010 IEEE International Conference on Nano/Molecular Medicine and Engineering. IEEE, 2010.) (Year: 2010).*

NPL Pullano et al (Pullano, Salvatore Andrea, et al. "Medical devices for pediatric apnea monitoring and therapy: past and new trends." IEEE reviews in biomedical engineering 10 (2017): 199-212.) (Year: 2017).*

NPL Toda et al (Toda, Hideki, and Genci Capi. "Development of a high resolution human breath gas sensor considering application for rescue robotics in disaster zones." 2010 IEEE International Workshop on Robotic and Sensors Environments. IEEE, 2010.) (Year: 2010).*

Extended European Search Report issued in Patent Application No. EP 18 17 5039 dated Jul. 20, 2018.

Japanese Office Action issued in Patent Application No. 2017-108750 dated Nov. 24, 2020.

Japanese Office Action issued in Patent Application No. 2017-108750 dated Jun. 22, 2021.

* cited by examiner

PHYSIOLOGICAL PARAMETER PROCESSING APPARATUS

CROSS REFERENCE TO RELATED APPLICATION

This application is based on Japanese Patent Applications No. 2017-108750 filed on May 31, 2017, the contents of which are incorporated herein by reference.

BACKGROUND

The present invention relates to a physiological parameter processing apparatus.

JP-T-2000-500379 discloses a respiratory monitoring device which relates to diagnosis of a sleep disorder, and which is configured by combining a pressure sensor that is in fluid communication with the nose of the patient, with a temperature sensor that operates so as to generate a signal indicating the temperature of the interior of the nose and that of the vicinity of the mouth of the patient.

SUMMARY

As the patient sleeps, the respiratory monitoring device of JP-T-2000-500379 continually monitors the breathing pattern for a predetermined period of time. Then, the outputs of the pressure sensor and the temperature sensor are analyzed in combination.

By the analysis, the respiratory monitoring device determines that the breathing of the patient has a normal breathing pattern, or that the breathing of the patient indicates a breathing disorder.

Situations where a measurement result is requested to be analyzed in real time, such as a case where the respiration of a postoperative patient is managed in a hospital are being increased in number. However, the respiratory monitoring device of JP-T-2000-500379 is configured so that breathing is monitored and then the frequency of occurrence of abnormal breathing and the like are analyzed, and therefore a measurement result is not analyzed in real time.

A physiological parameter processing apparatus which analyzes in real time a measurement result of a respiratory gas is provided.

The physiological parameter processing apparatus includes an input interface section that acquires respiration data produced based on a respiratory gas that is obtained from at least one of a mouth and nose of a subject, and an analyzing section that analyzes in real time the respiration data acquired through the input interface section, and that produces analysis result data which can be displayed in real time.

The configuration includes the analyzing section which produces analysis result data that may be displayed in real time, and therefore respiration data may be analyzed in real time. Moreover, the analysis result may be displayed in real time.

The physiological parameter processing apparatus of the disclosure may analyze in real time a measurement result of a respiratory gas.

DETAILED DESCRIPTION OF EMBODIMENTS

Figure 1:
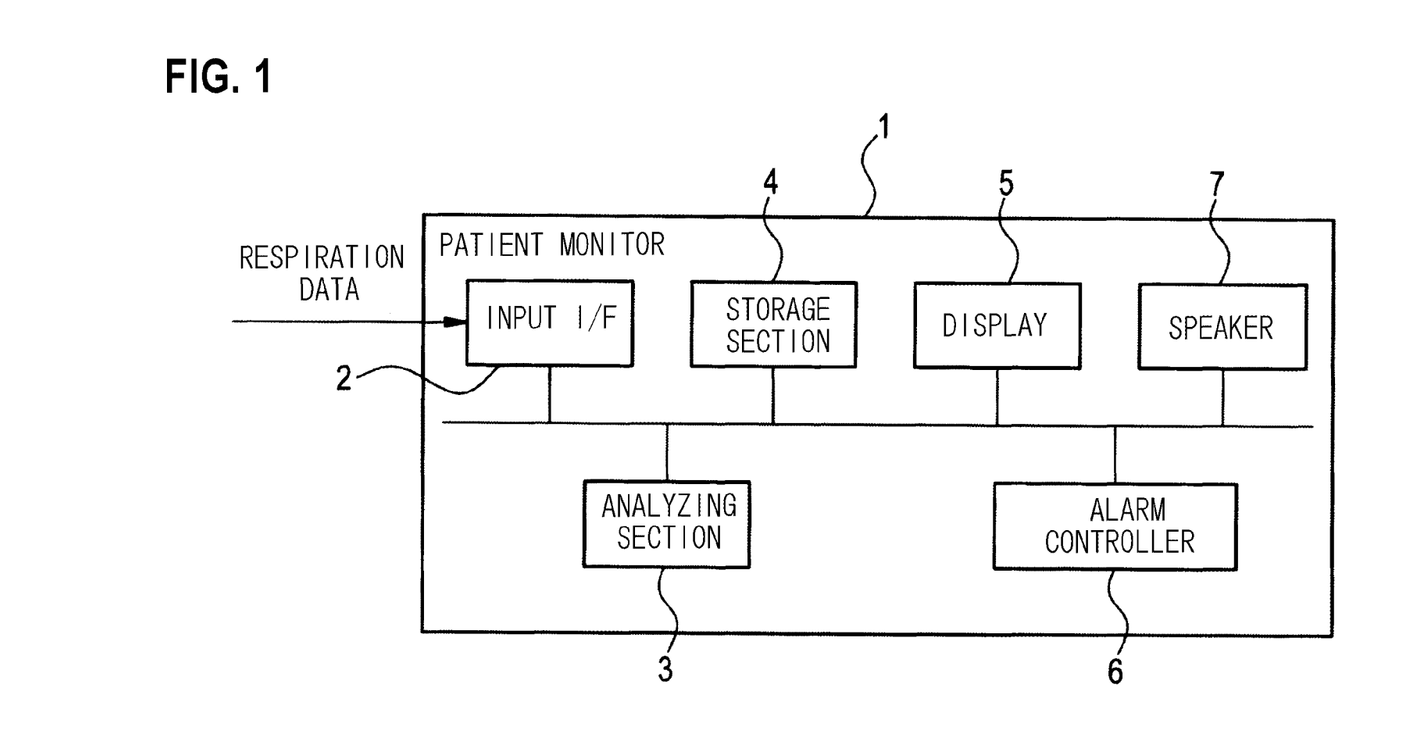
FIG. 1 is a conceptual diagram of a physiological parameter processing apparatus.

Hereinafter, an embodiment of the physiological parameter processing apparatus of the disclosure will be described with reference to the drawings. FIG. 1 is a conceptual diagram of a physiological parameter processing apparatus 1 of the embodiment of the disclosure.

The physiological parameter processing apparatus 1 is an apparatus for analyzing in real time a measurement result of a respiratory gas. As shown in FIG. 1, for example, the physiological parameter processing apparatus 1 is configured by including an input interface section 2, an analyzing section 3, a storage section 4, a display 5, an alarm controller 6, and a speaker 7. The display 5 is an example of a displaying section and the alarm controller 6 and the speaker 7 are example of a notifying section.

<Input Interface Section>

The input interface section (hereinafter, referred to as "input I/F") 2 is configured so as to acquire respiration data that are produced based on a respiratory gas which is obtained from at least one of the mouth and nose of the subject.

The respiratory gas consists of an expiration gas and inspiration gas of the subject, and exhibits vital signs information useful in analyzing the presence/absence of apnea, hypopnea, and upper airway occlusion. The respiration data acquired by the input I/F 2 contain detection results relating to a respiratory gas, such as the expiratory volume, the inspiratory volume, and detection time periods of these volumes. The respiration data are data which are produced from the respiratory gas. The respiratory gas is an example of measurement results of the subject. For example, the respiration data may be data relating to the air flow component, snore component, or the like which is produced by signal processing the respiratory pressure of the respiratory gas.

The input I/F 2 may be configured so as to acquire respiration data from various media. From a respiratory gas sensor using a cannula attached to at least one of the mouth and nose of the subject, the input I/F 2 may acquire respiration data which are analyzed and produced by the sensor, through a connector that connects the sensor with the physiological parameter processing apparatus 1. Alternatively, the input I/F 2 may be configured so as to acquire respiration data which is to be analyzed by the physiological parameter processing apparatus 1, through a wired or wireless communication network. The input I/F 2 is configured so as to output the acquired respiration data to the analyzing section 3.

The input I/F 2 may be configured so as to include various wired connection terminals for communicating with various media through a communication network, and various processing circuits for wireless connections, and meet communication standards for communicating through the communication network. Here, the communication network may be a LAN (Local Area Network), a WAN (Wide Area Network), the Internet, or the like. The input I/F 2 may be wirelessly connected to various media through access points, or in ad-hoc mode.

<Analyzing Section>

The analyzing section 3 is configured so as to analyze in real time the respiration data acquired from the input I/F 2, to produce analysis result data that may be displayed in real time.

Figure 2:
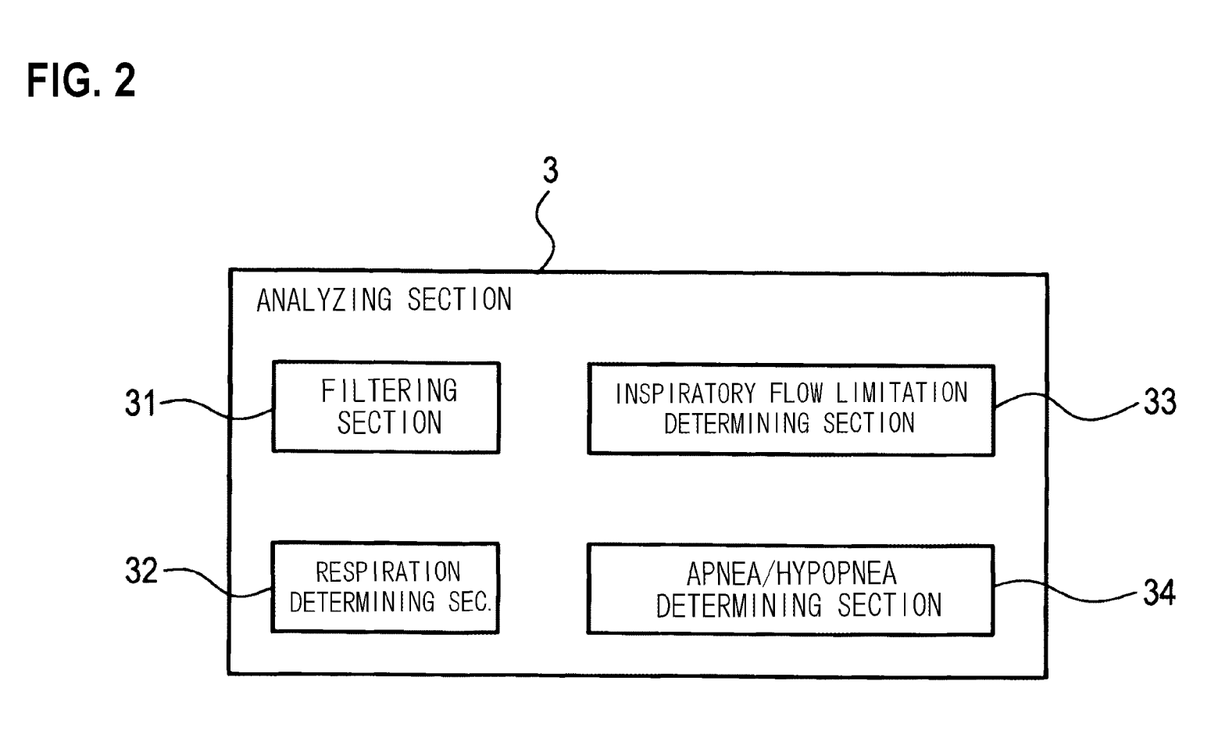
FIG. 2 is a diagram showing an example of the internal structure of an analyzing section.

The analyzing section 3 is configured so as to perform various analyzations relating to respiration data. FIG. 2 is a diagram showing an example of the internal structure of the analyzing section 3. As shown in FIG. 2, the analyzing section 3 includes a filtering section 31, a respiration determining section 32, an inspiratory flow limitation determining section 33, and an apnea/hypopnea determining section 34. Results of determinations which are performed by the filtering section 31, respiration determining section 32, inspiratory flow limitation determining section 33, and apnea/hypopnea determining section 34 in the analyzing section 3 are acquired and stored in the storage section, and supplied to the display 5 to be displayed thereon in real time.

For example, the analyzing section 3 may be configured by a controller which includes a memory and a processor. The memory is configured so as to store computer-readable commands (programs), and consists of a ROM (Read Only Memory) which stores various programs and the like, a RAM (Random Access Memory) having work areas in which various programs to be executed by the processor, and the like are stored, etc. The processor consists of, for example, a CPU (Central Processing Unit), a MPU (Micro Processing Unit), and/or a GPU (Graphics Processing Unit), and is configured so as to develop a designated one of the various programs incorporated in the ROM, in the RAM, and execute various processes in cooperation with the RAM.

<Filtering Section>

The filtering section 31 is configured so as to perform waveform processing on the respiration data. The waveform processing includes a process such as removal of components which are not required in analysis of the respiration data. For example, the waveform processing which is performed in the filtering section may be a process of removing noises from the respiration data, that of removing high-frequency components, that of removing low-frequency components, or that of performing the square root amplification or square root amplification correction on an AD value contained in the respiration data.

Alternatively, the filtering section 31 may be a digital filter. The digital filter may be configured so as to acquire a digital signal of the respiration data from the input I/F 2, and perform waveform processing on the signal. In the case where analog data are acquired through the input I/F 2, an A/D converter may be disposed in the filtering section 31.

The respiration data which have undergone the waveform processing are output to the storage section 4 and the display 5, and used in various analyses in the analyzing section 3.

<Respiration Determining Section>

Figure 5:
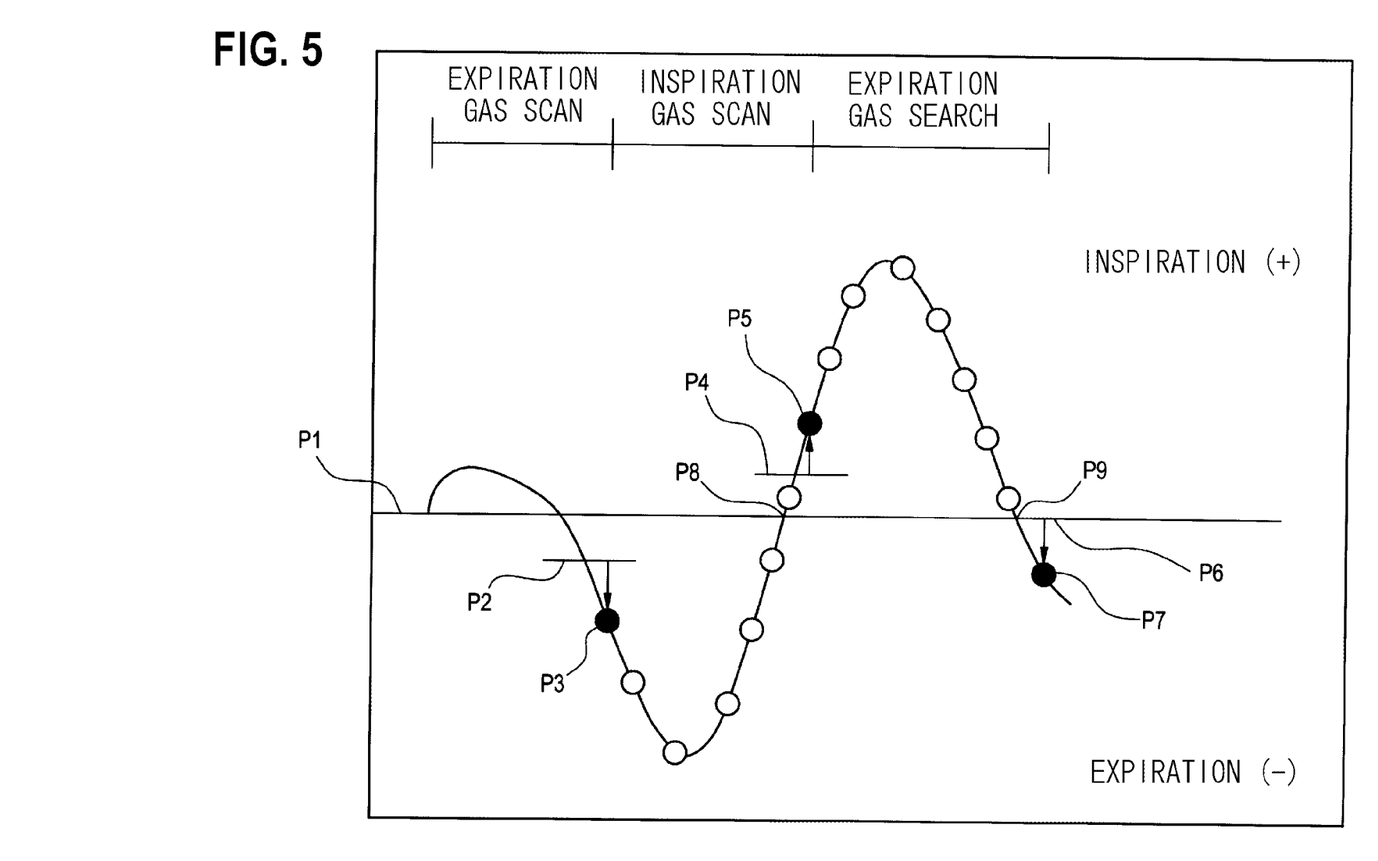
FIG. 5 illustrates an example of analysis of respiration data.

The respiration determining section 32 is configured so as to compare and analyze the respiration data and a first value relating to the respiratory gas in an expiration gas scan mode, an inspiration gas scan mode, and an expiration gas search mode. FIG. 5 is a view showing an example of analysis of respiration data in the expiration gas scan mode, the inspiration gas scan mode, and the expiration gas search mode.

As shown in FIG. 5, the expiration gas scan mode is a mode in which a second value P3 that is on the minus side of the first value P1 is detected, and the respiration data are scanned until expiration gas is detected. In a respiration waveform that is the respiration data, for example, a predetermined reference value of the respiration waveform is set as the first value P1, and a value which is equal to or smaller than an arbitrary value P2 that is on the minus side of the first value P1 is set as the second value P3. The expiration gas scan mode may be configured so that expiration gas is detected by detecting the second value P3.

The inspiration gas scan mode is a mode which is executed after the expiration gas scan mode to detect inspiration gas. For example, the inspiration gas scan mode may be configured so that, after the process of the expiration gas scan mode, a value which is equal to or larger than an arbitrary value P4 that is on the plus side of the first value P1 (the reference value of the respiration waveform) in the expiration gas scan mode is set as a third value P5, and inspiration gas is detected by detecting the third value P5.

The expiration gas search mode is a mode in which, after the process of the inspiration gas scan mode, expiration gas is detected, and the end point of the respiration waveform that is used in analyzation is searched. The expiration gas search mode may be configured so that, after the process of the inspiration gas scan mode, a value which is equal to or smaller than an arbitrary value P6 that is on the minus side of the first value P1 (the reference value of the respiration waveform) in the expiration gas scan mode is set as a fourth value P7, and expiration gas indicating the end point of the respiration waveform is detected by detecting the fourth value P7.

In an example of determination performed by the respiration determining section 32, with respect to the respiration waveform of respiration data in which expiration gas is minus, and inspiration gas is plus, the first value P1 is set to 0 mmH2O, the arbitrary value P2 that is in the expiration gas scan mode, and that is on the minus side of the first value P1 is set to −0.05 mmH2O, and −0.06 mmH2O which is the second value P3 is detected, thereby detecting expiration gas. The arbitrary value P4 that is in the inspiration gas scan mode, and that is on the plus side of the first value P1 is set to +0.2 mmH2O, and +0.25 mmH2O which is the third value P5 is detected, thereby detecting inspiration gas. The arbitrary value P6 that is in the expiration gas search mode, and that is equal to or smaller than the first value P1 is set to 0 mmH2O, and −0.01 mmH2O which is the forth value P7 is detected, thereby detecting expiration gas indicating the end point of the respiration waveform.

The respiration determining section 32 can calculate the respiration rate of the subject based on the numbers of expirations and inspirations which are detected during a predetermined period of time in the expiration gas scan mode, the inspiration gas scan mode, and the expiration gas search mode. In the case where the predetermined period of time is set to 30 seconds, for example, the number of sets of an expiration gas and inspiration gas that are detected in the expiration gas scan mode, the inspiration gas scan mode, and the expiration gas search mode is doubled, whereby the respiration rate for one minute can be calculated.

<Inspiratory Flow Limitation Determining Section>

The inspiratory flow limitation determining section 33 is configured so as to determine whether an inspiratory flow limitation is present or absent, based on the waveform of the inspiration gas in the respiration data. The inspiratory flow limitation is an index showing the obstructive apnea/hypopnea condition.

The inspiratory flow limitation determining section 33 is configured so as to determine the inspiratory flow limitation based on: the presence/absence of a predetermined shape in the inspiration gas waveform in the respiration data; and a ratio of the width of the inspiration gas waveform having the predetermined shape, and that of the waveform of the predetermined shape.

For example, the width of the inspiration gas waveform shows the zone between the value P8 at which the inspiration gas waveform indicated in FIG. 5 rises, and P9 at which the inspiration gas waveform ends. In the case where an inspiration gas waveform which is partly recessed is detected, for example, the inspiratory flow limitation determining section 33 determines whether an inspiratory flow limitation is present or absent, from the waveform width occupied by the recess of the inspiration gas waveform, in the width of the inspiration gas waveform containing the recess.

For example, the above-described detection of a recess can be performed in the following manner. The inspiration gas waveform is secondarily differentiated. When the calculation result (amplitude) of the secondary differentiation has a negative value, it is determined that there is a recess. In the case where, with respect to the width of the inspiration gas waveform, the waveform width of the detected recess exceeds a predetermined threshold, it can be determined that the inspiratory flow limitation is present.

The predetermined threshold can be appropriately set by the user in consideration of individual variation depending on the subject, and the operational standards of the facility.

The result of the determination performed by the inspiratory flow limitation determining section 33 is supplied to the storage section 4 and the display 5.

<Apnea/Hypopnea Determining Section>

When the amplitude of the respiration data during a predetermined period of time is equal to or lower than a predetermined ratio of the average amplitude, the apnea/hypopnea determining section 34 determines that apnea or hypopnea occurs.

Alternatively, the apnea/hypopnea determining section 34 may make the determination depending on whether the amplitude of the respiration data at a time zone in the immediate vicinity of the measurement time of the respiration data is equal to or lower than the predetermined ratio of the average amplitude or not. For example, the time zone in the immediate vicinity of the measurement time of the respiration data extends from 120 seconds before the measurement time to the measurement time. An example of the amplitude at which it is determined that apnea occurs is an amplitude which is equal to or lower than 10% of the average amplitude, and that at which it is determined that hypopnea occurs is an amplitude which is equal to or lower than 50% of the average amplitude.

<Storage Section>

The storage section 4 is configured so as to store analysis result data. The storage section 4 is configured so as to sequentially store the respiration data output from the filtering section 31, and the determination results of the determining sections 32 to 34, as analysis result data. The analysis result data stored in the storage section 4 are as required sent to the display 5 to be displayed thereon, and supplied to the alarm controller 6 to be used in determination of the necessity of notification. The storage section 4 may store also information relating to notification such as contents of abnormality notified from the notifying section, and the manner of the notification, as the notification history. The storage section 4 may be a memory configured by a ROM (Read Only Memory) which stores various programs and the like, a RAM (Random Access Memory) having work areas in which various programs to be executed by the processor, and the like are stored, etc.

<Displaying Section>

Figure 3:
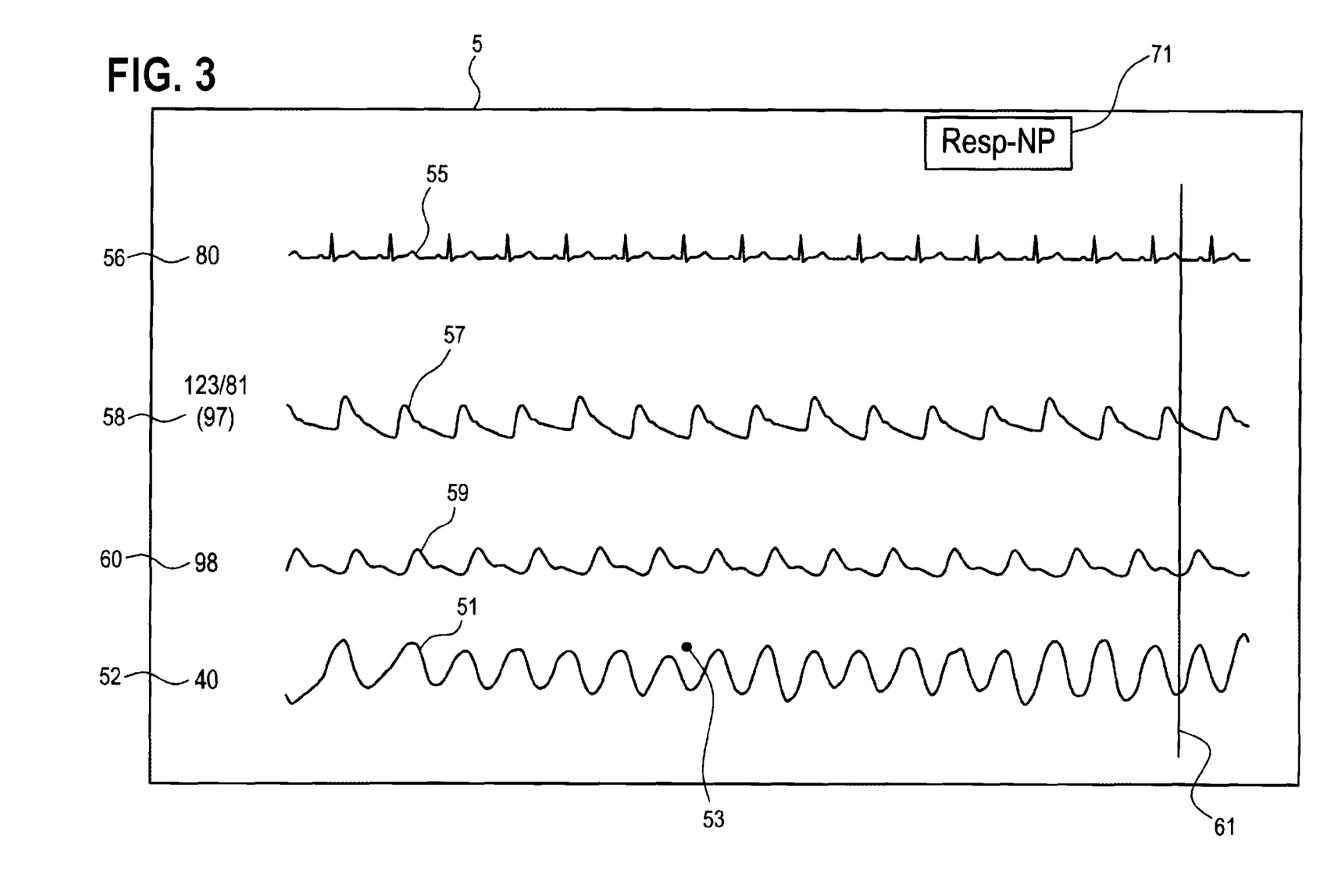
FIG. 3 illustrates an example of a display screen of the physiological parameter processing apparatus.

As shown in FIG. 1, the physiological parameter processing apparatus includes the displaying section which acquires at least real-time analysis result data from the analyzing section 3, and which displays the data. FIG. 3 is a view showing a display example of the display 5 which is an example of the displaying section. The respiration waveform 51 of the respiration data, "40" (referenced by 52) which is a numerical value indicating the respiration rate, and the inspiratory flow limitation waveform 53 are shown in the display 5 of FIG. 3.

Figure 4:
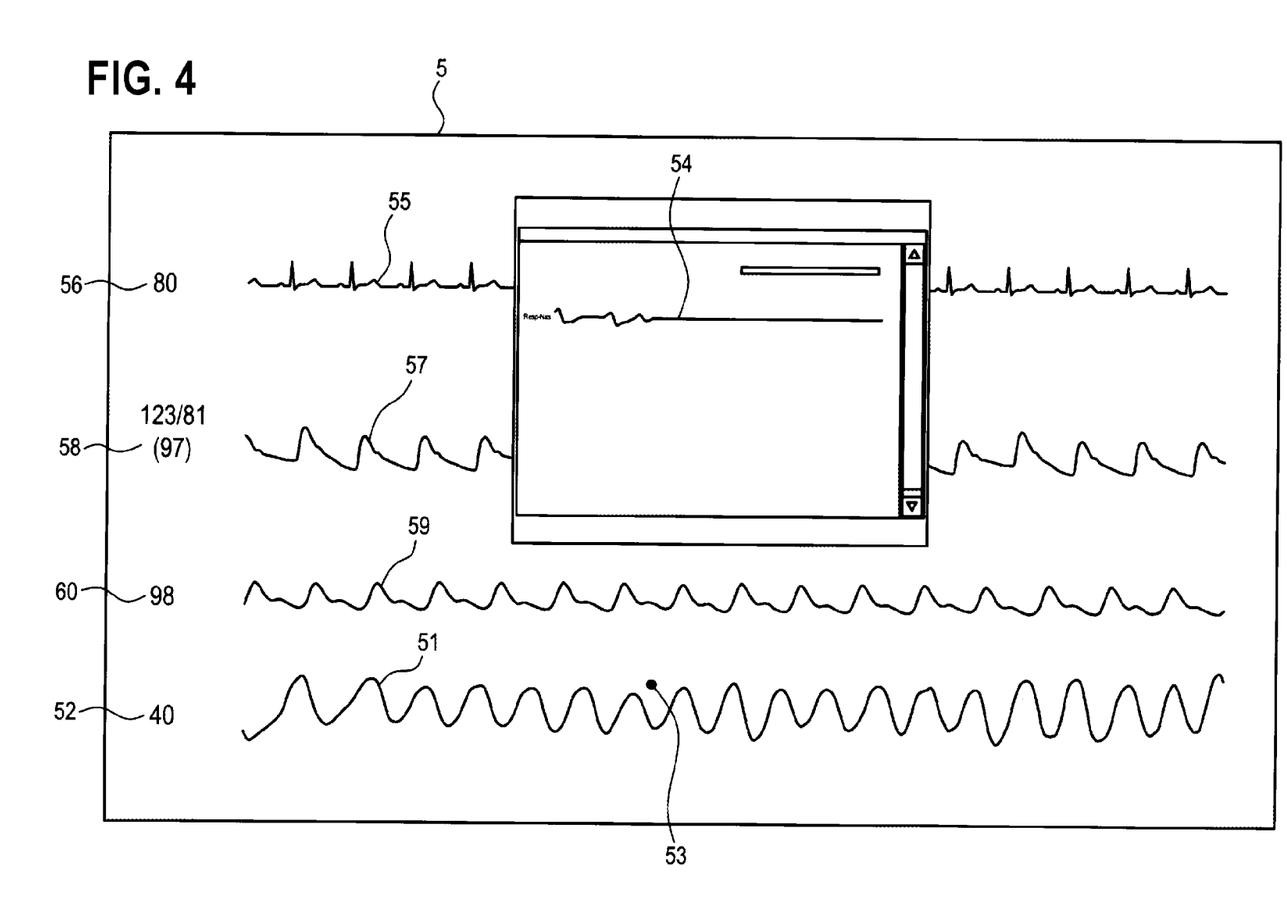
FIG. 4 illustrates another example of the display screen of the physiological parameter processing apparatus.

The display 5 may display in real time analysis result data which are obtained by acquiring the respiration data immediately after the measurement, and performing real-time analysis on the data, or display past (120 seconds prior to the display timing) analysis result data which are stored in the storage section 4. For example, the past analysis result data are in the form of a trend graph or a list of respiration data. FIG. 4 shows an example in which the respiration waveform 51 that is formed by displaying in real time the respiration data, and a respiration waveform 54 consisting of the past analysis result data are displayed on the display 5. In FIG. 4, a screen of the past analysis result data is displayed overlappingly on the real time display screen, the display manner is not limited to the example, and a plurality of screens may be displayed so as not to overlap with one another.

The display 5 may be configured so as to read out past notification information stored in the storage section 4, and display the information (review displayed). For example, the past notification information which is to be displayed on the display 5 includes a trend graph of respiration information, an alert condition, a vital list, or the like.

Also data other than analysis result data relating to the respiration data may be displayed on the display 5. Data to be displayed may be a plurality of kinds of vital signs information. For example, the plurality of kinds of vital signs information may be data of at least one of the transcutaneous arterial oxygen saturation, the heart rate, the blood pressure, and an electrocardiogram. The display may be configured so as to display these data in a state (in-phase) where a plurality of kinds of vital signs information acquired from the same subject are synchronized in phase with one another. FIG. 3 shows, in addition to the respiration waveform 51 of the respiration data, the waveform 55 of an electrocardiogram, "80" (referenced by 56) which indicates the heart rate, the waveform 57 of the blood pressure, "123/81(97)" (referenced by 58) which indicate the blood pressure values, the waveform 59 of the transcutaneous arterial oxygen saturation, and "98" (referenced by 60) which indicates the value of the transcutaneous arterial oxygen saturation. In FIG. 3, the reference numeral 61 indicates that the respiration waveform 51, the electrocardiogram waveform 55, the waveform 57 of the blood pressure, and the waveform 59 of the transcutaneous arterial oxygen saturation are in-phase.

<Notifying Section>

The physiological parameter processing apparatus 1 is configured so as to include the notifying section which notifies of the notification information based on the analysis result data. The notifying section is configured so as to, in the case where notification is necessary, such as that where a measurement result is abnormal, notify that an abnormality occurs. The notifying section includes the alarm controller 6 which is shown in FIG. 1, and the speaker 7 which notifies by voice of the contents of the notification. The notification of the notification information is not limited to that performed by sound produced by the speaker 7. In the case of visual notification, the notification information may be displayed on the display 5, or, when notification is necessary, a lamp may be lit on. As an example of visual notification, a notification displaying section 71 which displays the notification information by using characters is shown in the display 5 of FIG. 3.

The contents notified by the notifying section may be determination in which the apnea/hypopnea determining section 34 determines that apnea or hypopnea occurs, or that in which it is determined that an inspiratory flow limitation is present. The contents which are to be notified may include an abnormality relating to a measurement, such as that the cannula is detached and therefore respiration data cannot be acquired.

<Operation Example>

Next, an operation example of the physiological parameter processing apparatus 1 will be described.

The input I/F 2 of the physiological parameter processing apparatus 1 is connected to a sensor which detects the respiratory gas from the mouth or nose of the subject, and acquires respiration data from the sensor. The input I/F 2 supplies the acquired respiration data to the filtering section 31 of the analyzing section 3. The filtering section 31 performs waveform processing on the acquired respiration data. The filtering section 31 outputs the respiration data which have undergone the waveform processing, to the storage section 4. The storage section 4 stores the respiration data acquired from the filtering section 31.

The analyzing section 3 performs various analyses based on the respiration data acquired from the input I/F 2. The filtering section 31 of the analyzing section 3 outputs the respiration data which have undergone the waveform processing, to the respiration determining section 32, the inspiratory flow limitation determining section 33, and the apnea/hypopnea determining section 34. The respiration determining section 32 performs analyses relating to the respiration data and the respiratory gas in the expiration gas scan mode, the inspiration gas scan mode, and the expiration gas search mode, and determines the respiration rate. The inspiratory flow limitation determining section 33 determines the presence/absence of an inspiratory flow limitation. The apnea/hypopnea determining section 34 determines whether the apnea condition is present or not, and whether the hypopnea condition is present or not. The results of the determinations are supplied to the storage section 4 to be stored therein. Moreover, the determination results are displayed in real time on the display 5.

The alarm controller 6 acquires analysis result data from the analyzing section 3, and determines whether notification is necessary or not, based on the analysis result data. If it is determined that notification is necessary, the alarm controller 6 outputs notification information to the speaker 7. The speaker 7 converts the acquired notification information to sound, and outputs the sound. The output notification information is output also to the storage section 4 to be stored therein.

As described above, the physiological parameter processing apparatus 1 of the disclosure includes: the input interface section 2 which acquires respiration data that are produced based on the respiratory gas which is obtained from at least one of the mouth and nose of the subject; and the analyzing section 3 which analyzes in real time the respiration data acquired from the input interface section 2, and which produces analysis result data that can be displayed in real time. Therefore, the apparatus can analysis in real time the respiration data, and moreover display in real time the result of the analysis.

Conventionally, respiration monitoring is performed using an EtCO2 (End Tidal CO2) capnometer or the thoracic impedance method. An EtCO2 capnometer is a device which is used for measuring carbon dioxide contained in the respiratory gas, and has a matter that, when an airway is not secured, the measurement may be incorrect. An EtCO2 capnometer acquires a result of measurement of the respiratory gas in the form of a respiratory gas CO2 concentration curve (capnogram). In an EtCO2 capnometer, therefore, it is difficult to distinguish between hypopnea and hyperventilation, and also the respiration depth cannot be measured. An EtCO2 capnometer is insufficient for monitoring the respiration during the non-intubation period, and cannot perform a real-time analysis.

Among the conventional respiration monitoring methods, the thoracic impedance method is a method in which, when the respiration is to be measured, an AC current is flown through a portion where no action potential exists, and a resistance change in the body of the subject is detected as a voltage change. Therefore, the method is easily affected by noises due to motion artifacts of the subject. In the thoracic impedance method, moreover, it is impossible to distinguish a difference between the respiratory motion under the normal condition, and that under an abnormal condition. Consequently, the method cannot be sufficiently used in a respiration monitoring apparatus, and cannot perform a real-time analysis.

Most of postoperative respiratory complications are complications relating to upper airway occlusion. It is important for prevention of complications to confirm the presence/absence of upper airway occlusion. In the conventional respiration monitoring methods (an EtCO2 capnometer, the thoracic impedance method), however, it is not impossible to confirm the presence/absence of upper airway occlusion.

In order to check the presence/absence of upper airway occlusion, conventionally, a screening test using a sleep apnea test apparatus has been performed. In the screening test using a sleep apnea test apparatus, values of intranasal pressures are collected and analyzed to check the presence/absence of upper airway occlusion in the subject.

In the conventional screening test using a sleep apnea test apparatus, however, the collected values of intranasal pressures are not analyzed in real time, and there is no test apparatus for monitoring in real time the presence/absence of upper airway occlusion.

According to the physiological parameter processing apparatus 1 of the disclosure, a real-time analysis, which is impossible in the prior art, may be performed on a result of measurement of the respiratory gas, and moreover it is possible to check in real time the presence/absence of upper airway occlusion. Furthermore, a result of the analysis may be displayed in real time.

According to the physiological parameter processing apparatus 1 of the disclosure, moreover, the analyzing section 3 includes the filtering section 31 which performs waveform processing on the respiration data, and therefore analysis result data which may be displayed in real time is produced by using the filtering section 31. The analyzing section 3 analyzes the respiration data which have undergone the waveform processing in the filtering section 31. When the respiration data which have undergone the waveform processing in the filtering section 31 are analyzed, therefore, the analysis accuracy of real-time analysis of the respiration data is enhanced. The analyzing section 3 produces the respiration data which have undergone the waveform processing in the filtering section 31, as at least a part of the analysis result data, and therefore the respiration data which have undergone the waveform processing in the filtering section 31 may be displayed in real time.

The physiological parameter processing apparatus 1 of the disclosure includes the respiration determining section 32 which analyzes respiration data in the expiration gas scan mode, the inspiration gas scan mode, and the expiration gas search mode, and therefore can simply perform a real-time analysis on the respiration data. Moreover, analysis is performed in in the expiration gas scan mode, the inspiration gas scan mode, and the expiration gas search mode, and hence it is possible to determine the the respiration rate The physiological parameter processing apparatus 1 of the disclosure has the inspiratory flow limitation determining section 33 which determines an inspiratory flow limitation, and therefore may determine in real time the presence/absence of an inspiratory flow limitation. Moreover, a result of the determination of an inspiratory flow limitation may be displayed in real time.

In the physiological parameter processing apparatus 1 of the disclosure, the analyzing section 3 includes the apnea/hypopnea determining section 34 which determines one of at least apnea and hypopnea, and therefore it is possible to analyze in real time whether apnea occurs or not, and whether hypopnea occurs or not. Moreover, a result of the real-time analysis may be displayed in real time.

The physiological parameter processing apparatus 1 of the disclosure determines whether apnea or hypopnea occurs or not, based on the amplitude of the respiration data in the immediate vicinity of the measurement time of the respiration data, and hence may analyze in real time more accurately whether apnea or hypopnea occurs. A result of the real-time analysis is displayed.

The physiological parameter processing apparatus 1 of the disclosure includes the alarm controller 6 and the speaker 7 as the notifying section which notifies of the notification information, and hence surely notifies of the notification information such as apnea, hypopnea, and an inspiratory flow limitation, so that it is possible to appropriately cope with change in the condition of the subject.

The physiological parameter processing apparatus 1 of the disclosure includes the display 5 which displays analysis result data, and hence may display in real time an analysis result. Therefore, it is possible to rapidly perform medical decision support in respiratory management.

The physiological parameter processing apparatus 1 of the disclosure includes the storage section 4 which stores analysis result data, and therefore past analysis result data of the subject may be displayed.

According to the physiological parameter processing apparatus 1 of the disclosure, moreover, an analysis result and other vital signs information such as an electrocardiogram are displayed in phase with each other, and hence in-phase monitoring of the analysis result and the other vital signs information is enabled. With respect to various kinds of vital signs information including respiratory management, therefore, medical decision support is rapidly performed.

A configuration may be possible where, in addition to the physiological parameter processing apparatus 1 of the disclosure that displays in phase an analysis result and other vital signs information such as an electrocardiogram are displayed in phase with each other, an EtCO2 capnometer or thoracic impedance method, which is conventionally used, is employed. In the configuration where the physiological parameter processing apparatus 1 of the disclosure, and an EtCO2 capnometer or thoracic impedance method, which is conventionally used, are combinedly employed as described above, respiration monitoring during the non-intubation period, postoperative respiratory management, that during endoscopic gastrointestinal surgery, or that during nasal high flow is performed. Therefore, a configuration including respiratory monitoring of the pressure of the respiratory gas (the intranasal pressure) is realized, and it is possible to provide optimum respiratory monitoring according to the situation of the subject.

In the above configuration, the embodiment in which the input I/F 2 acquires respiration data from a sensor that is not shown has been described, the method of acquiring respiration data is not limited to the above-described configuration. The input I/F 2 may be connected to past respiration data (measurement results) which are stored in an external medium such as a CD-R, and acquire the past respiration data, or alternatively acquire in real time respiration data which are measured in real time in a remote place, by using a communication network.

According to the configuration, an external apparatus may be connected to the physiological parameter processing apparatus 1 through the Internet, and a measurement result of a respiratory gas may be displayed in real time on the display 5.

In the above configuration, the embodiment in which the physiological parameter processing apparatus 1 has the analyzing section 3 has been described, the invention is not limited to the configuration where the analyzing section 3 is included in the physiological parameter processing apparatus 1. A configuration may be employed where an analyzing section is disposed outside the physiological parameter processing apparatus 1, and respiration data produced in the external analyzing section are sent to the physiological parameter processing apparatus 1 through an input I/F to be displayed on the display 5.

The above-described configuration may include: an input interface section which acquires respiration data in which a real-time analysis is performed on respiration data that are produced based on a respiratory gas which is obtained from at least one of a mouth and nose of a subject; and a displaying section which may display in real time the respiration data that are acquired from the input interface section, and therefore a result of the real-time analysis of the respiration data may be displayed in real time.

The invention is not limited to the above-described embodiment and modifications, and may be adequately subjected to modifications, improvements, and the like. In addition, the materials, shapes, dimensions, values, forms, numbers, places, and the like of the components of the above-described embodiment are arbitrary and not limited insofar as the invention is achieved.

What is claimed is:

1. A physiological parameter processing apparatus comprising:
    an input interface configured to acquire respiration data produced based on a respiratory gas that is obtained from at least one of a mouth or nose of a subject, the input interface being connected to a respiratory gas sensor configured to acquire the respiration data;
    a processor configured to analyze in real time the respiration data acquired through the input interface, and to produce real-time analysis result data;
    a display configured to acquire the real-time analysis result data from the processor, and to display the real-time analysis result data in real-time; and a memory configured to store the real-time analysis result data, wherein the processor is configured to calculate a respiration rate of the subject based on respiration depth of the subject and a number of expirations and inspirations of the subject detected during a predetermined period of time, and to supply the calculated respiration rate to the display, wherein the predetermined period of time is within one minute, and wherein the display is configured to display:
  the respiration rate acquired from the processor as the real-time analysis result data,
  the real-time analysis result data and a waveform of the respiration data adjacent to each other on a primary screen, and
  past analysis result data acquired from the memory on a secondary screen.

2. The physiological parameter processing apparatus according to claim 1, wherein the processor is further configured to analyze the respiration data by waveform processing the respiration data.

3. The physiological parameter processing apparatus according to claim 2, wherein the waveform processing comprises filtering the respiration data.

4. The physiological parameter processing apparatus according to claim 2, wherein the analysis result data includes the respiration data after the waveform processing.

5. The physiological parameter processing apparatus according to claim 1, wherein the processor is further configured to analyze the respiration data by comparing the respiration data and a first value relating to the respiratory gas in:
  an expiration gas scan mode in which a second value that is on a minus side of the first value is detected;
  an inspiration gas scan mode in which, after the process of the expiration gas scan mode, a third value that is on a plus side of the first value is detected; and
  an expiration gas search mode in which, after the process of the inspiration gas scan mode, a fourth value that is on a minus side of the first value is detected.

6. The physiological parameter processing apparatus according to claim 1, wherein the processor is further configured to analyze the respiration data by determining an inspiratory flow limitation, based on:
  a presence or absence of a given shape in an inspiration gas waveform in the respiration data; and
  a ratio of a width of the inspiration gas waveform having the given shape, and a width of a standard waveform of the given shape.

7. The physiological parameter processing apparatus according to claim 1, wherein the processor is further configured to analyze the respiration data by determining at least one of apnea or hypopnea when an amplitude of expiration of the respiration data in the predetermined period of time is equal to or lower than a predetermined ratio of an average amplitude of the expiration of the respiration data.

8. The physiological parameter processing apparatus according to claim 7, wherein the processor is further configured to determine whether or not the amplitude of the expiration of the respiration data is equal to or lower than an amplitude corresponding to the predetermined ratio of the average amplitude of the expiration of the respiration data, based on the amplitude of the expiration of the respiration data in an immediate vicinity of a measurement time of the respiration data.

9. The physiological parameter processing apparatus according to claim 1, wherein the processor is further configured to output notification information based on the analysis result data.

10. The physiological parameter processing apparatus according to claim 1, wherein the display is further configured to display in real time the analysis result data and data of at least one of a transcutaneous arterial oxygen saturation, a heart rate, a blood pressure, or an electrocardiogram in phase with the analysis result data.

11. The physiological parameter processing apparatus according to claim 1, wherein the processor is further configured to output an alarm when the real-time analysis result data indicates an abnormal respiratory condition.

12. The physiological parameter processing apparatus according to claim 1, wherein the processor is further configured to check in real time, based on the real-time analysis result data, a presence or absence of upper airway occlusion of the subject to prevent complications relating thereto.

13. A physiological parameter processing apparatus comprising:
  an input interface configured to acquire respiration data produced based on a respiratory gas that is obtained from at least one of a mouth or nose of a subject, the input interface being connected to a respiratory gas sensor configured to acquire the respiration data;
  a processor configured to analyze in real time the respiration data acquired through the input interface, and to produce real-time analysis result data;
  a display configured to acquire the real-time analysis result data from the processor, and to display the real-time analysis result data in real-time; and
  a memory configured to store the real-time analysis result data,
  wherein the processor is configured to analyze the respiration data by comparing the respiration data and a first value relating to the respiratory gas to analyze the respiration data in:
    an expiration gas scan mode in which a second value that is on a minus side of the first value is detected;
    an inspiration gas scan mode in which, after the process of the expiration gas scan mode, a third value that is on a plus side of the first value is detected; and
    an expiration gas search mode in which, after the process of the inspiration gas scan mode, a fourth value that is on a minus side of the first value is detected, and
  wherein the processor is further configured to calculate a respiration rate of the subject based on a number of expirations and inspirations of the subject analyzed in the expiration gas scan mode, the inspiration gas scan mode, the expiration gas search mode, the number of expirations and inspirations of the subject being detected within one minute, and to supply the calculated respiration rate to the display,
  wherein the display is configured to display:
    the respiration rate acquired from the processor as the real-time analysis result data,
    the real-time analysis result data and a waveform of the respiration data adjacent to each other on a primary screen, and
    past analysis result data acquired from the memory on a secondary screen.

14. The physiological parameter processing apparatus according to claim 13, wherein the secondary screen overlaps the primary screen.

15. The physiological parameter processing apparatus according to claim 13, wherein the processor is further configured to output an alarm when the real-time analysis result data indicates an abnormal respiratory condition.

16. The physiological parameter processing apparatus according to claim 13, wherein the display is further configured to display in real time the analysis result data and data of at least one of a transcutaneous arterial oxygen saturation, a heart rate, a blood pressure, or an electrocardiogram in phase with the analysis result data.

17. The physiological parameter processing apparatus according to claim 13, wherein the processor is further configured to check in real time, based on the real-time analysis result data, a presence or absence of upper airway occlusion of the subject to prevent complications relating thereto.

* * * * *